United States Patent [19]

van der Vies

[11] 4,002,747

[45] Jan. 11, 1977

[54] NOVEL ESTER OF 19-NOR-TESTOSTERONE

[75] Inventor: Johannes van der Vies, Oss, Netherlands

[73] Assignee: Akzona Incorporated, Asheville, N.C.

[22] Filed: Nov. 24, 1975

[21] Appl. No.: 634,391

[30] Foreign Application Priority Data

Dec. 2, 1974 Netherlands .................. 7415669

[52] U.S. Cl. ........................... 424/243; 260/397.4
[51] Int. Cl.$^2$ ......................................... C07J 1/00
[58] Field of Search ............................ 260/397.4

[56] References Cited

FOREIGN PATENTS OR APPLICATIONS 1,149,256   4/1969   United Kingdom ............ 260/397.4

*Primary Examiner*—Elbert L. Roberts
*Attorney, Agent, or Firm*—Francis W. Young; Philip M. Pippenger; Hugo E. Weisberger

[57] ABSTRACT

The invention relates to a novel di-ester of 19-nor-testosterone and the preparation thereof. The novel di-ester, i.e. the 2′,2″-oxydiacetate, is a strong anabolic agent.

2 Claims, No Drawings

NOVEL ESTER OF 19-NOR-TESTOSTERONE

The novel di-ester may be prepared by reacting 19-nor-testosterone with 2',2''-oxy-diacetic acid

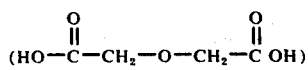

or a functional derivative thereof, for example the di-halide. For that purpose 19-nor-testosterone may be reacted with the free di-carboxylic acid in the presence of a dehydrating agent. Usually the esterification is carried out with the dihalide of the di-carboxylic acid, preferably the dichloride

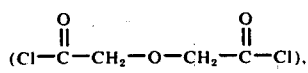

in a solvent in the presence of a base, for example in pyridine/acetone. Instead of pyridine, also picoline or collidine may be used. Other suitable solvents that may be used in combination with the said amines are chloroform, methylene chloride, carbon tetrachloride, benzene, hexane, methylethylketone, dioxane and tetrahydrofuran. If these solvents are not used in combination with an amine, the HCl formed can be bound with sodium or potassium hydroxide. The reaction is usually performed at a temperature between 0° and 30° C, if desired also at a higher temperature.

The novel di-ester is usually administered parenterally, for example intramuscularly or subcutaneously, in a suitable vehicle.

The injection liquid is usually prepared by dissolving or suspending the di-ester in a vegetable oil, such as arachis oil, sesame oil, olive oil or castor oil, if desired in combination with auxiliaries, such as antiseptics, solubilisation agents and/or surfactants, such as benzyl alcohol, benzyl benzoate, etc.

The concentration of the di-ester in the injection liquid usually is between 10 and 50 mg/cm$^3$.

The novel ester has a strong anabolic activity and a favourable ratio of anabolic and androgenic activity, which is illustrated by the following comparative tests.

MLA-TEST ACCORDING TO HERSHBERGER

A single dose of the substance to be tested was administered to male rats in the form of a subcutaneous injection of the substance in oil. After one week the increase in % by weight of the M. levator ani (M.L.A.) was determined. This increase in weight is a measure of the anabolic activity. Further the increase in weight of the seminal vesicle and the ventral prostate were determined (androgenic activity). The figures found have been listed in table A.

Table A

| Compound | M.L.A. | Seminal vesicle | Ventral prostate |
|---|---|---|---|
| 1 × 0.5 mg; 1 week | increase in weight in wt % with regard to controls | | |
| di-nandrolone-2',2''-oxy-diacetate | 111 | 141 | 170 |
| nandrolone-phenylpropionate | 98 | 179 | 228 |

From table A follows that the novel ester has only a slightly higher anabolic activity than the known ester nandrolone-phenylpropionate; however, the androgenic activity is clearly lower.

From the relative anabolic and androgenic activity of the novel ester with regard to nandrolone-phenylpropionate, determined in extensive trials, wherein also lower and higher dosages were tested and moreover the increases in weight were not only determined after one week but also after two and three weeks, the so-called relative Q-values (in relation to nandrolone-phenylpropionate) were calculated. These Q-values have been listed in table B.

Table B

| di-nandrolone-2',2''-oxy-diacetate | Q-value in relation to nandrolone-phenylpropionate | |
|---|---|---|
| | with respect to seminal vesicle | with respect to ventral prostate |
| after 1 week | 1,2 | 1,3 |
| after 2 weeks | 1,5 | 1,1 |
| after 3 weeks | 1,9 | 1,4 |

The Q-value of an anabolic agent is the ratio of the anabolic and androgenic potency. The Q-value is therefore a criterion for the dissociation between anabolic and androgenic activity.

For the significance of the Q-value for anabolics reference is made to "Sheffield Symposium on Cytotoxic Agents and Anabolic Steroids", 10 November 1966, The Parcener Press Ltd., London (1967), pages 11–25, and to G. A. Overbeek, "Anabolic Steroids", Springer Verlag (1966), pages 24–36.

The absolute Q-value of an anabolic compound says but little of the therapeutical value of this compound. Of much more importance for the therapeutical value is the relative Q-value with regard to a known anabolic agent, such as nandrolone-phenylpropionate. From table B it follows that for the novel nandrolone ester, the relative Q-value in relation to nandrolone-phenylpropionate is in all tests greater than 1 which implies that the novel ester is superior to nandrolone-phenylpropionate.

The biological activity of nandrolone esters is due to the activity of the "free" steroid nandrolone on the receptor (Acta Endocrinologa 49 (1965), pages 271–282). With regard to the biological availability of the active component the resorption-velocity from the subcutaneous or intramuscular depot and the velocity of hydrolysis of the ester in the plasma (Acta Endocrinologica 64 (1970), pages 656–669) are of importance in this connection.

From comparative "in vitro" tests in rat plasma and human plasma it turned out that the novel di-ester is hydrolysed more rapidly than nandrolone-phenylpropionate which means that at equal plasma-concentrations of said esters, the minimal effective plasma concentration of nandrolone in the case of the novel di-ester is attained more rapidly than in the case of nandrolone-phenylpropionate.

Moreover it turned out that the distribution-coefficient of the novel di-ester in the two-phases system methanol/arachis oil is greater than that of nandrolone-phenylpropionate, which points to a more rapid resorption of the novel di-ester from the intramuscular depot. Nevertheless the novel di-ester appears to possess an excellent protracted activity.

The fact that the novel di-ester hydrolyses in human plasma (which is a prerequisite for being active), is all the more surprising because structurally related di-esters, such as di-nandrolone-succinate and di-nandrolone-glutarate, do not or hardly hydrolyse in human plasma and therefore are inactive or hardly active.

The invention is illustrated by the following examples:

EXAMPLE 1

In a mixture of 8 ml of dry pyridine and 5 ml of dry acetone 5 g of 17β-hydroxy-Δ⁴-estren-3-one were dissolved. After cooling down to 0° C, a solution of 1,4 ml of diglycolic acid dichloride in 2 ml of dry acetone was added dropwise in 25 minutes. The reaction mixture was stirred at room temperature for 3 hours whereafter an additional amount of 0.5 ml of diglycolic acid dichloride was added. The reaction mixture was stirred for one hour and then poured out into water.

The crystals were filtered off, washed with water, dried and then crystallised from methanol, giving 5,5 g of 1′,1″-di(3-oxo-17β-hydroxy-Δ⁴-estren-17β-yl)-2′,2″-oxydi-acetate with a melting point of 190°–193° C and $[\alpha]_D^{20} = +55°$ (in chloroform).

EXAMPLE 2

Some examples of pharmaceutical preparations, containing the di-ester of Example 1.

| | | | |
|---|---|---|---|
| a) | Di-ester | 10 | mg |
| | Benzylalcohol | 0.05 | cm³ |
| | Purified arachis oil to | 1 | cm³ |
| b) | Di-ester | 25 | mg |
| | Benzylbenzoate | 0.46 | cm³ |
| | Benzylalcohol | 0.05 | cm³ |
| | Purified arachis oil to | 1 | cm³ |

I claim:
1. The compound, having the formula:

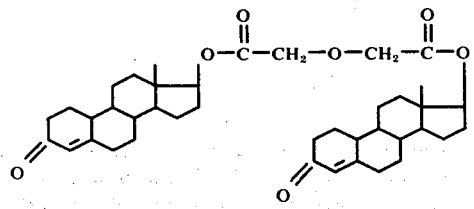

2. A pharmaceutical composition adapted for parenteral administration comprising the compound of claim 1 in a concentration from about 10 to about 50 mg per cc. in a pharmaceutically acceptable liquid carrier.

* * * * *